United States Patent [19]

Eberlein et al.

[11] Patent Number: 5,610,155

[45] Date of Patent: Mar. 11, 1997

[54] CONDENSED DIAZEPINONES, PROCESSES FOR PREPARING THEM AND AGENTS CONTAINING THESE COMPOUNDS FOR TREATING DISEASES OF THE CENTRAL NERVOUS SYSTEM AND FOR PROMOTING CEREBRAL BLOOD CIRCULATION

[75] Inventors: Wolfgang Eberlein; Gerhard Mihm; Wolfhard Engel; Klaus Rudolf, all of Biberach; Henri Doods, Warthausen; Harald Ziegler, Biberach; Michael Entzeroth, Warthausen, all of Germany

[73] Assignee: Dr. Karl Thomae GmbH, Biberach an der Riss, Germany

[21] Appl. No.: 457,061

[22] Filed: Jun. 1, 1995

Related U.S. Application Data

[62] Division of Ser. No. 421,108, Apr. 13, 1995, which is a continuation of Ser. No. 287,574, Aug. 9, 1994, abandoned, which is a continuation of Ser. No. 134,332, Oct. 12, 1993, abandoned, which is a continuation of Ser. No. 865,575, Apr. 9, 1992, abandoned.

[51] Int. Cl.⁶ .................. A61K 31/55; C07D 243/10
[52] U.S. Cl. .................................. 514/220; 540/495
[58] Field of Search ........................ 514/220; 540/495

[56] References Cited

U.S. PATENT DOCUMENTS

| 4,816,456 | 3/1989 | Summers | 514/255 |
| 5,175,158 | 12/1992 | Eberlein et al. | 514/220 |

FOREIGN PATENT DOCUMENTS

| 2018582 | 10/1990 | Canada. |
| 0312895 | 4/1989 | European Pat. Off.. |

OTHER PUBLICATIONS

Murray et al., Psychopharmacology, 1991, 105:134–136.
Doods et al., Life Sciences, vol. 52, pp. 497–503, 1993.

*Primary Examiner*—Yogendra N. Gupta

*Attorney, Agent, or Firm*—Robert P. Raymond; Alan R. Stempel; Mary-Ellen M. Devlin

[57] ABSTRACT

New condensed diazepinones of general formula I

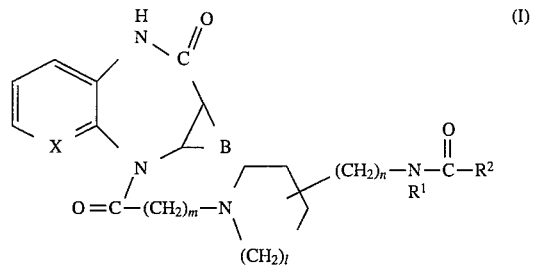

wherein B represents one of the divalent groups

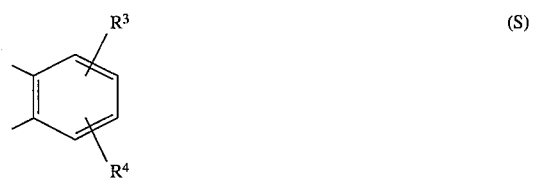

(S)

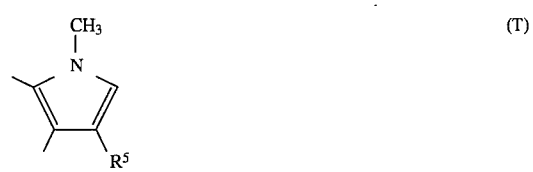

(T)

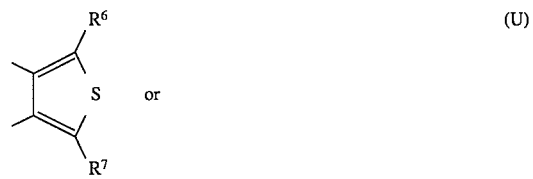

(U)

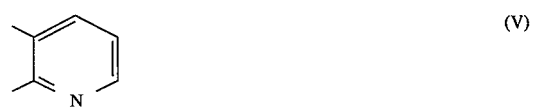

(V)

and X, l, m, n and $R^1$ to $R^7$ are as defined herein, as well as the salts thereof with inorganic or organic acids and processes for preparing them.

These compounds are useful for improving or normalising arteriosclerotically induced disorders of cerebral blood flow, for treating diseases of the central nervous system, particularly Alzheimer's disease and Parkinson's disease, and as vagal pacemakers for treating bradycardia and bradyarrhythmia, and also for improving memory performance.

6 Claims, 1 Drawing Sheet

FIG. 1

—□— YOUNG ANIMALS (PHYSIOL. SALINE SOLUTION)

—■— OLD, LEARNING IMPAIRED ANIMALS (PHYSIOL. SALINE SOLUTION)

—○— OLD, LEARNING IMPAIRED ANIMALS TREATED WITH 0.2 mg/kg OF SUBSTANCE D ADMINISTERED SUB-CUTANEOUSLY

CONDENSED DIAZEPINONES, PROCESSES FOR PREPARING THEM AND AGENTS CONTAINING THESE COMPOUNDS FOR TREATING DISEASES OF THE CENTRAL NERVOUS SYSTEM AND FOR PROMOTING CEREBRAL BLOOD CIRCULATION

This is a division of application Ser. No. 421,108, filed Apr. 13, 1995, which is a continuation of application Ser. No. 287,574, filed Aug. 9, 1994, now abandoned, which is a continuation of application Ser. No. 134,332, filed Oct. 12, 1993, now abandoned, which is a continuation of application Ser. No. 865,575, filed Apr. 9, 1992, now abandoned.

The invention relates to new condensed diazepinones, processes for preparing them and agents containing these compounds for treating diseases of the central nervous system and for promoting cerebral blood flow.

Condensed diazepinones with anti-ulcerative properties and an inhibitory effect on gastric juice secretion are already known from EP-A-39519 and 57428 and from U.S. Pat. Nos. 3660380; 3,691,159; 4,213,984; 4,213,985; 4,210,648; 4,410,527; 4,424,225; 4,424,222 and 4,424,226.

With reference to condensed diazepinones, EP-A-156191 (U.S. Pat. No. 4,550,107) and EP-A-312895 describe how completely different pharmacological properties compared with the compounds of the above-mentioned publications, namely favourable effects on heart rate, can be induced by introducing alkylaminoacyl or dialkylaminoacyl groups. This is also true of the compounds of EP-A-213293, EP-A-254955, EP-A-273239, EP-A-306698, DE-A-3800986, DE-A-3802334, DE-A-3819444, DE-A-3820346 and DE-A-3820345. The compounds of these publications are suitable for use as vagal pacemakers for treating bradycardia and bradyarrhythmia in human and veterinary medicine on account of their favourable effects on hear rate and in the light of their lack of inhibitory effects on gastric juice secretion and salivation and their lack of mydriatic effects. EP-A2-402734 describes condensed diazepinones as agents for treating diseases of the central nervous system and for promoting cerebral blood flow. These agents are suitable for use in geriatrics and for treating migraine. A number of the compounds described therein demonstrate good CNS-availability and can therefore be used for treating diseases of the central nervous system, particularly Alzheimer's disease.

According to the structure-activity equations derived hitherto, the presence of a terminal basic N-atom in the side chain is found to be essential for muscarinic antagonists with a high $M_2$-selectivity (cf. U.S. Pat. No. 4,550,107, EP-A2-402734 and Engel et al. in J. Med. Chem. 32: 1718 (1989)).

Surprisingly, it has now been found that by acylating the terminal basic nitrogen atom of the side chain bound to the amino nitrogen of the diazepinone ring, $M_2$-selective muscarinic antagonists with a high affinity can be obtained.

The "carboxamides" according to the invention also demonstrate a substantially better $M_2/M_1$-ratio, compared with the $M_2$-selective antagonists described hitherto, i.e. the new compounds exhibit a substantially more favourable ratio of bonding affinity relative to $M_2$-receptors than to $M_1$-receptors.

In view of their $M_2$-selectivity the compounds according to the invention can be used for treating bradycardia and bradyarrhythmia in human and veterinary medicine. In the light of their favourable effects on cerebral blood flow the compounds are particularly suitable for use in geriatrics and for treating migraine. As has been found in animal experiments (on the rat) they increase the learning capacity of old animals.

The new condensed diazepinones according to the invention are highly lipophilic, in some cases, and therefore satisfy an essential prerequisite for good cerebro-availability. At the same time this high lipophilicity results in a rapid drop in the blood level, which means that there is no effect on heart rate. $M_2$-selective antagonists which have a favourable CNS-penetration and at the same time have an $M_2/M_1$-selectivity are particularly suitable for treating diseases of the central nervous system, especially Alzheimer's disease.

The condensed diazepinones according to the invention have the general formula I wherein B represents one of the divalent groups and X, l, m, n and $R^1$ to $R^7$ are defined as follows:

X is a =CH— group or, if B represents the divalent group (S), X may also represent a nitrogen atom;

l is an integer 1, 2 or 3;

m is an integer 1 or 2;

n is an integer from 1 to 4;

$R^1$ is a hydrogen atom or a straight-chained or branched $C_{1-6}$alkyl group, $R^2$ is a hydrogen atom, a straight-chained or branched $C_{1-8}$alkyl group, a straight-chained or branched $C_{4-6}$alkenyl group, a $C_{3-7}$cycloalkyl group optionally substituted by a $C_{1-3}$alkyl group, an adamantyl group, a phenyl group optionally substituted by one or two methyl or methoxy groups or by a halogen atom, or a phenylalkyl group having 1 to 3 carbon atoms in the alkylene moiety optionally substituted by a methyl or methoxy group or by a halogen atom at the aromatic group, $R^3$ and $R^4$, which may be identical or different, are hydrogen or halogen atoms or methyl, ethyl, methoxy or ethoxy groups;

$R^5$ is a hydrogen or chlorine atom or a methyl group, $R_6$ and $R^7$, which may be identical or different, represent hydrogen atoms or $C_{1-3}$alkyl groups, but $R^7$ may additionally represent a halogen atom.

Preferred compounds of general formula I above are those wherein

X is a nitrogen atom,

B is the divalent group (S), l is the number 2, m is the number 1, n represents the number 3 or 4, $R^1$ is a straight-chained $C_{1-4}$alkyl group, $R^2$ is a branched $C_{4-6}$alkyl group, a cyclopropyl, cyclobutyl, cyclopentyl, cyclohexyl, cycloheptyl, methylcyclopentyl, methylcyclohexyl, methylcycloheptyl or adamantyl group, $R^3$ and $R^4$ represent hydrogen atoms or one of these groups represents a methyl group or a halogen atom and the substituent $-(CH_2)_n-NR_1-CO-R^2$ is connected to the 4-position of the piperidinyl ring.

Particularly preferred compounds are those wherein $R^1$ represents an ethyl group.

Examples of branched alkyl or alkenyl groups include the 1-methyl-ethyl, 1,1-dimethyl-ethyl, 1,1-dimethyl-propyl, 1,1-dimethyl-butyl, 1,1,3-trimethyl-butyl, 1-ethyl-1-methyl-ethyl, 1-ethyl-1-methyl-propyl, 1-ethyl-1-methyl-butyl, 1-ethyl-1,3-dimethyl-butyl, 1-propyl-1-methyl-ethyl, 1-propyl-1-methyl-propyl, 1-propyl-1-methyl-butyl, 1-ethyl-ethyl, 1,1-diethyl-ethyl, 1,1-diethyl-propyl, 1,1-dimethyl-butyl and 1,1-dimethyl-but-3-enyl groups.

The invention also relates to the acid addition salts with inorganic or organic acids, e.g. with hydrochloric acid, hydrobromic acid, sulphuric acid, fumaric acid, maleic acid, malic acid, citric acid, tartaric acid.

According to the invention, the new acylated diazepinones of general formula I are obtained by the following methods:

a) by reacting base-substituted condensed diazepinones of general formula II (II)

wherein X, B, l, m, n and $R^1$ are defined as hereinbefore, with carboxylic acids of general formula III (III)

wherein $R^2$ is defined as hereinbefore, or with the reactive derivatives thereof.

Examples of reactive derivatives of a carboxylic acid or general formula III include the esters thereof such as the methyl, ethyl or benzylester, the thioesters such as the methylthio or ethylthioester, the halides such as the acid chloride, the anhydrides and imidazolides thereof.

The reaction is conveniently carried out in a solvent such as methylene chloride, chloroform, carbon tetrachloride, ether, tetrahydrofuran, dioxane, benzene, toluene, acetonitrile or dimethylformamide, optionally in the presence of an acid activating agent or a dehydrating agent, e.g. in the presence of ethylchloroformate, thionyl chloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, and optionally in the presence of an inorganic base such as sodium carbonate or a tertiary organic base such as triethylamine or pyridine which may simultaneously be used as solvent, at temperatures between −25° and 150° C., but preferably at temperatures between −10° C. and the boiling temperature of the solvent used. The reaction may also be carried out without a solvent and furthermore any water formed during the reaction may be separated off by azeotropic distillation, e.g. by heating with toluene using a water separator or by the addition of a drying agent such as magnesium sulphate or molecular sieve.

For example, the reaction may be carried out with an acid halide in inert solvents such as ether, toluene, methylene chloride and the like, at temperatures between −50° C. and up to the boiling point of the reaction mixture, preferably between 0° C. and 50° C., and preferably in the presence of a hydrogen halide-binding agent, e.g. a tertiary amine, sodium carbonate or calcium carbonate. Not only the free amines of general formula II may be used but also the salts thereof from which the amines are liberated in situ by the auxiliary bases added.

The reactions may, for example, be carried out in the presence of imidazolides or carbodiimides in a high boiling solvent such as xylene at reflux temperature.

b) By acylating diazepinones of general formula IV (IV)

wherein X and B are as hereinbefore defined, with carboxylic acid derivatives of general formula V (V)

wherein l, m, n, $R^1$ and $R^2$ are as hereinbefore defined and Nu represents a nucleofugic group or leaving group.

The reaction of the compounds of general formula IV with the acid derivatives of general formula V is carried out in a known manner. The leaving group Nu is a group which forms a reactive carboxylic acid derivative together with the carbonyl group to which it is bound. Examples of reactive carboxylic acid derivatives include acid halides, esters, anhydrides or mixed anhydrides such as are formed from salts of the corresponding acids (Nu=OH) and acid chlorides, such as phosphorus-oxychloride, diphosphoric acid tetrachloride or chloroformic acid esters or the N-alkyl-2-acyloxypyridinium salts formed when compounds of general formula V (Nu=OH) are reacted with N-alkyl-2-halopyridinium salts.

Preferably, the reaction is carried out with the mixed anhydrides of strong inorganic acids, particularly dichlorophosphoric acid. The reaction may optionally be carried out in he presence of an acid-binding agent (proton acceptor). Examples of suitable proton acceptors are alkali metal carbonates or hydrogen carbonates such as sodium carbonate or potassium hydrogen carbonate; tertiary organic amines such as pyridine, triethylamine, ethyl diisopropylamine, 4-(dimethylamino)pyridine or sodium hydride. The reaction is carried out at temperatures between −25° C. and 130° C. in an inert solvent. Examples of inert solvents include chlorinated aliphatic hydrocarbons such as methylene chloride, 1,2-dichloroethane; open-chained or cyclic ethers such as diethylether, tetrahydrofuran or 1,4-dioxane; aromatic hydrocarbons such as benzene, toluene, xylene, o-dichlorobenzene; polar aprotic solvents such as acetonitrile, dimethylformamide or hexamethyl-phosphoric acid triamide; or mixtures thereof. The reaction times range from 15 minutes to 80 hours, depending on the type and quantity of acylating agent of general formula V used. It is not necessary to prepare the compounds of general formula V in pure form; instead, they may be produced in situ in the reaction mixture in a known manner.

The bases of general formula I thus obtained may subsequently be converted into the acid addition salts thereof or, if acid addition salts are obtained, they may be converted into the free bases or other pharmacologically acceptable acid addition salts.

The new condensed diazepinones of general formula I according to the invention contain up to two independent chiral carbon atoms. The acylated tricyclic compound itself can be regarded as a further chiral element, which may occur in two mirror-symmetrical forms. The nature of the tricyclic compound determines whether the energy barrier for inversion at this centre is so high that the individual isomers are stable at room temperature and capable of being isolated. It has been found that, in compounds of general formula I wherein X is a nitrogen atom and the positions adjacent to the diazepinone ring are unsubstituted, the activating energy required is reduced to such an extent that diastereomers can no longer be detected, let alone preparatively isolated, at room temperature.

The new condensed diazepinones of general formula I according to the invention thus contain up to three chiral elements, one of which is not structurally stable at ambient temperature under certain circumstances. Compounds of this kind may therefore occur in numerous diastereomeric forms and/or as enantiomeric (+)- and (−)-forms. The invention includes the individual isomers as well as the mixtures thereof. The diastereomers can be separated on the basis of their different physico-chemical properties, e.g. by fractional recrystallisation from suitable solvents, by high pressure liquid chromatography, column chromatography or gas chromatography.

Any racemates of the compounds of general formula I may be cleaved by known methods, for example using an optically active acid such as (−)- or (−)-tartaric acid or a derivative thereof such as (+)- or (−)-diacetyltartaric acid, (+)- or (−)-monomethyltartrate or (+)-camphorsulphonic acid.

According to a conventional method of enantiomer separation, the racemate of a compound of general formula I is reacted with one of the above-mentioned optically active acids in equimolar amounts in a solvent and the crystalline diastereomeric salts obtained are separated on the basis of their different solubilities. This reaction may be carried out in any kind of solvent provided that it shows a sufficiently great difference in the solubilities of the salts. It is preferable to use methanol, ethanol or mixtures thereof, e.g. in a ratio by volume of 50:50. Then each of the optically active salts is dissolved in water, neutralised with a base such as sodium carbonate or potassium carbonate and in this way the corresponding free compound is obtained in the (+)- or (−)-form.

Only one enantiomer or a mixture of two optically active diastereomeric compounds of general formula I is obtained if the methods of synthesis described above are carried out with only one corresponding enantiomer.

A starting compound of general formula II may be prepared as follows, for example:
an (aminoalkyl)pyridine of general formula VI wherein n and $R^1$ are as hereinbefore defined (compounds of this kind are known from the literature and can, in some cases, be obtained commercially) is tert.-butoxycarbonylated in a known manner, thus forming compounds of general formula VII:

Catalytic hydrogenation of these compounds by known methods, e.g. in ethanolic-hydrochloric acid solution and using platinum (IV)-oxide as catalyst (of. F. F. Blicke et al., J. Org. Chemistry 26: 3258 (1961)) or in glacial acetic acid in the presence of platinum (IV)-oxide (of. W. F. Minor et al., J. Med. Pharm. Chem. 5: 96, 105ff (1962) and A. H. Sommers et al., J. Amer. Chem. Soc. 75: 57, 58ff (1953)) yields compounds of general formula VIII:

a compound of this kind is subsequently reacted with a haloacyl compound of general formula IX wherein X, B and m are defined as hereinbefore and Hal represents a chlorine, bromine or iodine atom.

This amination is effected in an inert solvent at temperatures between −10° C. and the boiling temperature of the solvent, preferably either with at least 2 moles of secondary amine of general formula VIII or with 1 to 2 moles of the secondary amine of general formula VIII and an auxiliary base. Examples of solvents include chlorinated hydrocarbons such as methylene chloride, chloroform or dichloroethane; open-chained or cyclic ethers, such as diethylether, tetrahydrofuran or dioxane; aromatic hydrocarbons such as benzene, toluene, xylene, chlorobenzene or pyridine; alcohols such as ethanol or isopropanol; ketones such as acetone;

acetonitrile, dimethylformamide or 1,3-dimethyl-2-imidazolidinone. Examples of auxiliary bases include tertiary organic bases such as triethylamine, N-methylpiperidine, diethylaniline, pyridine and 4-(dimethylamino)pyridine or inorganic bases such as alkali metal or alkaline earth metal carbonates or hydrogen carbonates, hydroxides or oxides. If desired, the reaction may be accelerated by the addition of alkali metal iodides.

In this way, a compound of general formula X is obtained wherein the groups D, X, $R^1$ and m and n are as hereinbefore defined and from which the tert.-butoxycarbonyl group is cleaved in a known manner, e.g. using hydrobromic acid in glacial acetic acid, thereby forming a compound of general formula II.

The activated carboxylic acids of formula III are expediently obtained in the reaction mixture by methods known from the literature.

The diazepinones of general formula IV are known from the literature (of. EP-A-39519; EP-A-57428; DE-C-1179943 and 1204680; F. Hunzicker et al., Arzneim.-Forsch. 13: 324 (1965)).

The carboxylic acid derivatives of general formula V wherein Nu represents an alkoxy group are obtained by reacting substituted piperidines of general formula VIII with corresponding haloalkanoic acid esters, optionally using additional auxiliary bases, e.g. triethylamine, or catalysts, e.g. Triton B. By saponifying the resulting esters, e.g. using barium hydroxide solution, the carboxylic acids of general formula V wherein Nu represents a hydroxy group are obtained. The carboxylic acids obtained in this way then serve as starting substances for preparing derivatives with other nucleofugic groups, e.g. the acid halides of formula V.

The invention further relates to pharmaceutical compositions which contain one or more condensed diazepinones of general formula I or the physiologically acceptable salts thereof.

For this purpose, the compounds of general formula I may be incorporated in conventional pharmaceutical preparations in known manner, e.g. in solutions, suppositories, plain or coated tablets, capsules or infusions. The daily dose is generally between 0.02 and 5 mg/kg, preferably between 0.02 and 2.5 mg/kg, more particularly 0.05 and 1.0 mg/kg of body weight, administered optionally in the form of several, preferably 1 to 3, single doses, in order to achieve the desired results.

As already mentioned hereinbefore, the base-substituted condensed diazepinones of general formula I and the acid addition salts thereof have valuable properties; thus, they have favourable selectivity for cardiac $M_2$-receptors and can therefore be used as vagal pacemakers for treating bradycardia and bradyarrhythmia in both human and veterinary medicine.

It is known from investigations made by van Charldorp and van Zwieten (of. K. J. van Charldorp, Dissertation "Characterisation of Muscarinic Receptors in the Vascular System", Amsterdam 1988; K. J. van Charldorp, D. Davidesko and P. A. van Zwieten, Eur. J. Pharmacol. 150: 197–199 (1988); K. J. van Charldorp and P. A. van Zwieten, Naunyn Schmiedeberg's Arch. Pharmacol. 339: 403–408 (1989)) that the muscarinic receptors in the basilar arteries which are responsible for contraction of the blood vessels are of the $M_2$-type. It can therefor be expected that $M_2$-antagonists will relax the cerebral blood vessel and thereby increase blood flow.

Inhibition of the muscarinic receptors detectable in the cerebral blood vessels thus results in a prevention of constriction and an improvement or normalisation of the arteriosclerotically-induced disorders of cerebral blood flow. The new compounds according to the invention are particularly suitable for improving or normalising arteriosclerotically induced disorders of cerebral blood flow.

A number of compounds of general formula I exhibit good CNS-availability, owing to their high lipophilicity, and are therefore additionally suitable for the treatment of disease of the central nervous system, particularly Alzheimer's disease. In senile dementia of the Alzheimer's type, the degeneration of cholinergic neurones, particularly in hippocampal and cortical projections, leads to a reduced release of the neurotransmitter acetylcholine. The blockade of the presynaptic autoreceptors then interrupts the negative feedback mechanism which the neurotransmitter exerts on the still intact neurones and thereby brings about an increased release of acetylcholine and, consequently, stimulation of the post-synaptic receptors (D. C. Mash, D. L. Flynn and L. T. Potter, Science 228: 115–117 (1985); E. K. Perry et. al., Can. J. Neurol. Sci. 13: 521–527 (1986); M. Sarter et. al., TINS 11: 13–17 (1988)). The compounds are therefore suitable for use in geriatrics and significantly improve learning capacity and capacity for attention.

In order to demonstrate the favourable effects on cerebral blood flow the following trials were carried out:

A Studies of Binding to Muscarinic Receptors

Male Wistar rats (Chbb: THOM strain, 180–220 g body weight) were killed by a blow to the back of the neck. The cerebral cortex, heart and salivary glands were removed, washed and homogenised in a 20-fold volume of HEPES-buffer (20 mM 4-(2hydroxyethyl)-1-piperazino-ethanesulphonic acid, 100 mM sodium chloride, 10 mM magnesium chloride, pH 7.5) using an Ultra-Turrax apparatus at a maximum speed of rotation of 60 s. The homogenised matter was diluted to 1:500, based on the original quantity of tissue. For the binding test, 1 nM of [$^3$H]pirenzepine (3.22 TBq/mmol) which binds to $M_1$-receptors of the cortex and 0.3 nM of [$^3$H]NMS ($^3$H-N-methylscopolamine) (2.64 TBq/mmol) for binding to the heart and salivary glands was incubated at ambient temperature, for [$^3$H]pirenzepine for 90 minutes, for [$^3$H]NMS for 40 minutes, in each case with 0.35, 0.30 and 0.20 mg of protein per sample (0.5 ml) for heart, salivary gland and cortex. The protein concentration was determined by the method of Lowry et al. (J. Biol. Chem. 93: 265). Incubation was ended by rapid filtration through a glass fibre filter mat an using a Skatron Cell Harvester. After washing twice (for 10 seconds with about 3 ml of liquid) the filters were dried in the air, packed into mini vials, shaken overnight with 4 ml of scintillation liquid and the scintillation was counted with an efficiency of 45–50% using a Packard 460C apparatus. All the tests were carried out three times. The non-specific binding was defined as the radioactivity in the presence of 1 µM of (−)-3-quinuclidinyl-benzylate. The binding data were analysed by a computer-aided non-linear least square curve fitting method (Heinzel, G. 1982, in: Pharmacokinetics during Drug Development: Data Analysis and Evaluation Techniques, eds. G. Bozler and J. M. van Rossum (Gustav-Springer-Verlag), page 207). The dissociation constants Ki were calculated from the $IC_{50}$ values according to Cheny and Prusoff (Biochem. Pharmacol. 22: 3099 (1973)). The results are shown in Table 1.

B Investigation for Central Activity

Principle:

Arecoline has both a central and a peripherally active component. The peripheral (hypotensive) effects are blocked by N-methylscopolamine so that only the central (hypertensive) effect of arecoline occurs. Cerebroavailable antimuscarinics block this central effect.

Method:

Male rats weighing 300 g are anaesthetised i.p. with urethane (1.2 g/kg). The trachea is incubated, the animals are respirated with an air/oxygen mixture (80 breaths per minute). The blood pressure is recorded after canulation of the carotid artery by means of a pressure recorder (Bell and Howell Type 4-327-I). The test substances are administered through the jugular vein (0.5 mol/kg). Before the start of the trial the animals are given 0.5 mg/kg of N-methyl-scopolamine. The arecoline is administered (in doses of 0.3 mg/kg) at 15 minute intervals. After 2 comparison values, the test substance is injected in increasing doses 5 minutes before the next administration of arecoline.

The results obtained were compared with the average starting values and determined as the percentage inhibition. Table 2 contains the values found in the arecoline test.

C Effect on the Memory in the Morris Water Maze

The tests were carried out using the water maze described by R. G. M. Morris in Learn Motive 12: 239–249 (1981) using the test method described therein.

On the first day, rats which were 24 months old and therefore learning-impaired (n=7 per group) were given 0.2 mg/kg of compound D by subcutaneous route whilst another group of these animals were given physiological saline solution (s.c.). The groups were observed in the Morris water maze for 4 days.

Figure 1:
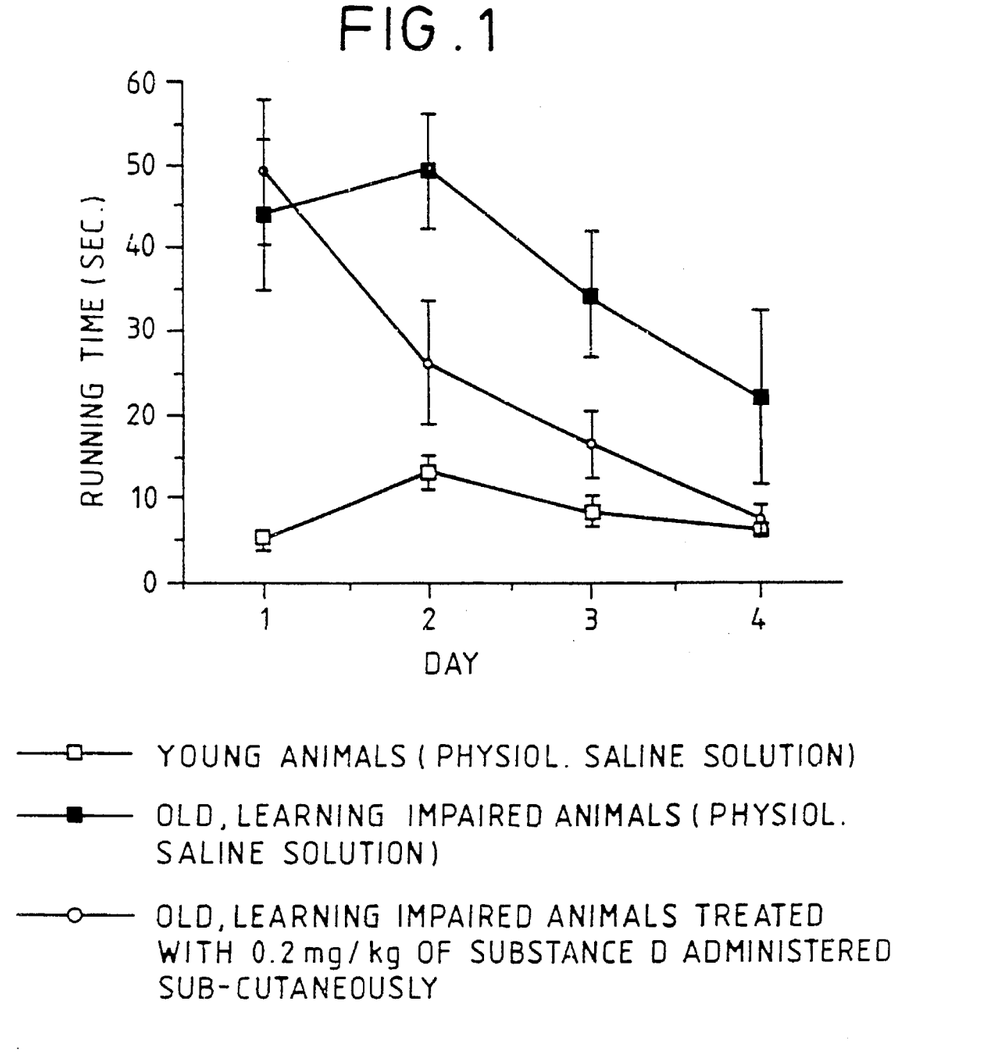

As is apparent from the path of the curves shown in FIG. 1, administration of compound D results in an improved memory performance compared with the animals which were learning-impaired on account of their age and were treated only with physiological saline solution. Thus, for example, on the second day the latency period was reduced by approximately 50%. On the fourth day the animals treated with substance D reached the same level as the control groups of young rats (n=7 per group) which were treated only with physiological saline solution. This effect of the $M_2$-antagonists according to the invention is surprising because, after administration of the $M_1$-selective antagonist pirenzepine, a deterioration in learning ability and memory performance was observed (A. J. Hunter and F. F. Roberts, Pharmacol. Biochem. and Behavior Vol. 30: 519–523 (1988), Title: "The effects of pirenzepine on spatial learning in the Morris Water Maze"). Similar negative observations after the administration of non-selective substances such as scopolamine or atropine are also reported by A. J. Hunter, F. F. Roberts and C. A. Tutty in Br. J. Pharmacol. 87: 41P (1986); R. J. Sutherland, I. Q. Wishaw and J. C. Regehr, J. Comp. Physiol. Psychol. 96: 563–573 (1982) and I. Q. Wishaw, Behav. Neurosci. 99: 979–1005 (1985).

By way of example the following compounds were investigated using the methods described above:

A=5,11-dihydro-11-[[4-[3-[(2,2-dimethyl-1-oxobutyl]-ethylamino]-propyl]-1-piperidinyl]acetyl]-6H-pyrido[2,3-b][1,4]benzodiazepin-6-one B=5,11-dihydro-[[4-[3-[(2,2-dimethyl-1-oxopentyl)-ethylamino]-propyl]-1-piperidinyl]acetyl]-6H-pyrido[2,3-b][1,4]benzodiazepin-6-one C=5,11-dihydro-11-[[4-[4-[(2,2-dimethyl-1-oxopentyl)-ethylamino]butyl]-1-piperidinyl]acetyl]-6H -pyrido[2,3-b][1,4]benzodiazepin-6-one D=5,11-dihydro-8-chloro-11-[[4-[3-[(2,2-dimethyl-1-oxopentyl)-ethylamino]propyl]-1-piperidinyl]-acetyl]-6H-pyrido[2,3-b][1,4]benzodiazepin-6-one E=5,11-dihydro-8-methyl-11-[[4-[3-[(2,2-dimethyl-1-oxopropyl)-ethylamino]propyl]-1-piperidinyl]acetyl]-6H-pyrido[2,3-b][1,4]benzodiazepin-6-one F=5,11-dihydro-11-[[4-[3-[(2,2-dimethyl-1-oxopropyl)-ethylamino]-1-piperidinyl]acetyl]-6H-pyrido[2,3-b][1,4]benzodiazepin-6-one G=5,11-dihydro-8-methyl-11-[[4-[3-[(2,2-dimethyl-1oxobutyl)ethylamino]propyl]-1-piperidinyl]acetyl]-6H-pyrido[2,3-b][1,4]benzodiazepin-6-one and these compounds were compared with the following known substances:

H=11-[[2-[(diethylamino)methyl]-1-piperidinyl]acetyl]-5,11-dihydro-6H-pyrido[2,3-b][1,4]benzodiazepin-6-one (see U.S. Pat. No. 4,550,107)

I=11-[[4-[4-(diethylamino)butyl]-1-piperidinyl]-acetyl]-5,11-dihydro-6H-pyrido[2,3-b][1,4]-benzodiazepin-6-one (see EP-A2-312895)

from EP-A1-402734:

J=5,11-dihydro-11-[1-oxo-6-(1-piperidinyl)-4-hexyn-1-yl]-6H-pyrido[2,3-b][1,4]benzodiazepin-6-one K=(±)-9-chloro-11-[[2-[(diethylamino)methyl]-1-piperidinyl]-acetyl]-5,11-dihydro-6H-pyrido[2,3-b]-[1,4]benzodiazepin-6-one L=5,11-dihydro-11-[[[2-[2-[(dipropylamino)methyl]-1-piperidinyl]ethyl]amino]carbonyl]-6H-pyrido[2,3-b]-[1,4]benzodiazepin-6-one methanesulphonate M=5,11-dihydro-11-[[3-[3-(1-piperidinyl)-1-propyl]-1piperidinyl]carbonyl]-6H-pyrido[2,3-b][1,4]benzo-diazepin-6-one N=4,9-dihydro-3-methyl-4-[[4-[3-(1-piperidinyl)-1-propyl]-1-piperidinyl]acetyl]-10H-thieno[3,4-b]-[1,5]benzodiazepin-10-one O=5,11-dihydro-11-[1-oxo-6-(1-piperidinyl)-1-hexyl]-6H-pyrido[2,3-b][1,4]benzodiazepin-10-one P=4,9-dihydro-3-methyl-4-[6-(hexahydro-1H-1-azepinyl)-1-oxo-4-hexyn-1-yl]-10H-thieno[3,4-b][1,5]ben-zodi-azepin-10-one Q=11-[4-[3-[(diethylamino)methyl]-4-morpholinyl]-1-oxo-1-butyl]-5,11-dihydro-6H-pyrido[2,3-b][1,4]-benzodiazepin-6-one R=5,11-dihydro-11-[[[2-(1-methyl-2-pyrrolidinyl)-ethyl]-methylamino]acetyl]-6H-pyrido[2,3-b][1,4]benzodi-azepin-6-one S=5,11-dihydro-11-[[[2-(1-methyl-hexahydro-1H-2-azepinyl)-ethyl]methylamino]acetyl]-6H-pyrido[2,3-b][1,4]benzodiazepin-6-one The results are shown in Tables 1 and 2 which follow:

TABLE 1

Receptor binding tests, in vitro: Results:

Receptor Binding Tests

| Substance | Ki [nM] $M_1$ (Cortex) | $M_2$ (Heart) | $M_3$ (Submandibular gland) | Selectivity ratio ($M_1/M_2$) |
|---|---|---|---|---|
| A | 500 | 25 | 750 | 20 |
| B | 150 | 15 | 300 | 10 |
| C | 500 | 38 | 875 | 13 |
| D | 866 | 25 | 916 | 35 |
| E | 1000 | 100 | 1500 | 10 |
| F | 900 | 65 | 1500 | 14 |
| G | 600 | 25 | 750 | 24 |
| H | 500 | 79 | 1995 | 6 |
| I | 20 | 5 | 151 | 4 |
| J | 794 | 120 | 1820 | 6.6 |
| K | 126 | 25 | 759 | 5 |
| L | 30 | 7.9 | 100 | 3.8 |
| M | 13 | 2 | 13 | 6.5 |
| N | 7.9 | 2 | 6 | 4 |
| O | 10 | 5 | 40 | 2 |
| P | 35 | 7.6 | 30 | 4.6 |
| Q | 50 | 20 | 50 | 2.5 |
| R | 7.1 | 3 | 30 | 2.4 |
| S | 16 | 3 | 25 | 5.3 |

TABLE 2

CNS-penetration, in vivo (rat)

| Substance ED$_{50}$ | [mg/kg] reduction in the arecoline-induced increase in blood pressure |
|---|---|
| A | 4.5 |
| B | 1.3 |
| C | 2.0 |
| D | 5.0 |
| E | 2.8 |
| F | 6.5 |
| G | 5.1 |
| H | >10.0 |
| K | >10.0 |
| L | >10.0 |
| O | >10.0 |

As is shown in Table 1, the specified compounds A to G exhibit excellent $M_1/M_2$-selectivity in the range from 10–35. This ratio demonstrates that the compounds specified are highly $M_2$-selective and are therefore capable of blocking presynaptic $M_2$-receptors in the brain, at a dosage at which $M_1$-receptors are unaffected. By contrast, the comparison substances H to S show only moderately marked $M_1/M_2$-selectivities with a selectivity ratio <6.6. A comparison of these selectivity values shows that the new diazepinones of general formula I are far superior to the comparison substances.

An essential prerequisite for the suitability of the compounds for treating CNS-diseases is the cerebro-availability of the substances. The test model described above for demonstrating CNS-penetration clearly shows (see Table 2) that substances A to G are capable of inhibiting the arecoline-mediated central effects. This finding can only be explained on the basis of good CNS-availability. By contrast, the comparison substances H, K, L and O tested with ED$_{50}$ values greater than 10 mg/kg (i.v.) had no effect on the increase in blood pressure caused by arecoline. This clearly demonstrates that these compounds have substantially worse penetration into the central nervous system.

The following Examples are intended to illustrate the invention:

EXAMPLE 1

5,11-Dihydro-11-[[4-[3-[2,2-dimethyl-1-oxobutyl)-ethylamino]-propyl]-1-piperidinyl]acetyl]-6H-pyrido[2,3-b][1,4]benzodiazepin-6-one 1.48 g (0.01 mol) of 2,2-dimethylbutyric acid chloride dissolved in 20 ml of tetrahydrofuran are added dropwise, with stirring, at ambient temperature, to a solution of 4.2 g (0.01 mol) of 5,11-dihydro-11-[[4-[3-(ethylamino)propyl]-1-piperidinyl]acetyl]-6H-pyrido-[2,3-b][1,4]benzodiazepin-6-one and 2 ml of triethylamine in 150 ml of tetrahydrofuran. In order to complete the reaction the solution is stirred for a further hour at 50° C. After cooling, the precipitated triethylamine hydrochloride is filtered off and the filtrate is evaporated to dryness using a rotary evaporator in a water jet vacuum. In order to purify it the residue is dissolved in ethyl acetate. The ethyl acetate solution is extracted twice with 10% hydrochloric acid, the organic phase is separated off and the aqueous phase is made alkaline by the addition of concentrated ammonia. Then the aqueous phase is extracted twice with ethyl acetate. The organic phase is dried over sodium sulphate and evaporated to dryness in vacuo. The residue obtained is crystallised by digesting it in ethyl acetate. Colourless crystals are obtained of m.p. 136°–138° C.

Yield: 2.4 g (46.2% of theory).

EXAMPLE 2

5,11-Dihydro-11-[[4-[3-[(benzoyl)ethylamino]propyl]-1-piperidinyl]acetyl]-6H-pyrido[2,3-b][1,4]benzodiazepin-6-one dihydrochloride Prepared analogously to Example 1 from 5,11-dihydro-11-[[4-[3-(ethylamino)propyl]-1-piperidinyl]acetyl]-6H-pyrido[2,3-b][1,4]benzodiazepin-6-one and benzoic acid chloride. The free base is dissolved in ethyl acetate and the dihydrochloride is precipitated by the addition of ethereal hydrochloric acid. The desired compound is obtained in a yield of 62% by recrystallisation from ethanol.

Colourless crystals of m.p. 152°–154° C. (ethanol).

EXAMPLE 3

5,11-Dihydro-11-[[4-[3-[(4-methoxybenzoyl)ethylamino]-propyl]-1-piperidinyl]acetyl]-6H-pyrido[2,3-b][1,4]-benzodiazepin-6-one dihydrochloride Prepared analogously to Example 1 from 5,11-dihydro-11-[[4-[3-(ethylamino)propyl]-1-piperidinyl]acetyl]-6H-pyrido[2,3-b][1,4]benzodiazepin-6-one and 4-methoxybenzoic acid chloride. The free base is dissolved in ethyl acetate and the dihydrochloride is precipitated by the addition of ethereal hydrochloric acid. The desired compound is obtained in a yield of 81% by recrystallisation from ethanol.

Colourless crystals of m.p. 163°–165° C. (ethanol).

EXAMPLE 4

5,11-Dihydro-11-[[4-[3-[(3,4-dimethoxybenzoyl)ethylamino]-propyl]1-piperidinyl]acetyl]-6H-pyrido[2,3-b]-[1,4] benzodiazepin-6-one dihydrochloride Prepared analogously to Example 1 from 5,11-dihydro-11-[[4-[3(ethylamino)propyl]-1-piperidinyl]acetyl]-6H-pyrido[2,3-b][1,4]benzodiazepin-6-one and 3,4-dimethoxybenzoic acid chloride. The free base is dissolved in ethyl acetate and the dihydrochloride is precipitated by the addition of ethereal hydrochloric acid.

Yield: 78% of theory.
Colourless crystals of m.p. 160°–162° C. (ethanol).

EXAMPLE 5

5,11-Dihydro-11-[[4-[3-[(phenylacetyl)ethylamino]-propyl]-1-piperidinyl]acetyl]-6H-pyrido[2 3-b][1,4-benzodiazepin-6-one dihydrochloride Prepared analogously to Example 1 from 5,11-dihydro-11-[[4-[3(ethylamino)propyl]-1-piperidinyl]acetyl]-6H-pyrido[2,3-b][1,4]benzodiazepin-6-one and phenylacetyl chloride. The free base is purified by chromatography on silica gel (Merck, 30–60 μm) using a mixture of ethyl acetate/methanol (98:2) as eluant and is then converted into the dihydrochloride by treating with ethereal hydrochloric acid.
Yield: 24% of theory.
Colourless crystals of m.p. 149°–152° C. (ethanol).

EXAMPLE 6

5,11-Dihydro-11-[[4-[3-[(acetyl)ethylamino]propyl]-1-piperidinyl]acetyl]-6H-pyrido[2,3-b][1,4]benzodiazepin-6-one Prepared analogously to Example 1 from 5,11-dihydro-11-[[4-[3(ethylamino)propyl]-1-piperidinyl]acetyl]-6H-pyrido[2,3-b][1,4]benzodiazepin-6-one and acetyl chloride in a yield of 56% of theory.
Colourless crystals of m.p. 178°–180° C. (ethyl acetate).

EXAMPLE 7

5,11-Dihydro-11-[[4-[3-[(2,2-dimethyl-1-oxopropyl)ethylamino]propyl]-1-piperidinyl]acetyl]-6H-pyrido[2,3-b][1,4]benzodiazepin-6-one Prepared analogously to Example 1 from 5,11-dihydro-11-[[4-[3-(ethylamino)propyl]-1-piperidinyl]acetyl]-6H-pyrido[2,3-b][1,4]benzodiazepin-6-one and pivalic acid chloride in a yield of 61% of theory.
Colourless crystals of m.p. 154°–155° C. (ethyl acetate).

EXAMPLE 8

5,11-Dihydro-11-[[2-[2-[(benzoyl)methylamino]ethyl]-1-piperidinyl]acetyl]-6H-pyrido[2,3-b][1,4]benzodiazepin-6-one A mixture of 9.5 g (0.033 mol) of 11-(chloroacetyl)-5,11-dihydro-6H-pyrido[2,3-b][1,4]benzodiazepin-6-one, 9.8 g (0.04 mol) of 2-[2-[(benzoyl)methylamino]ethyl]-piperidine, 4.2 g (0.04 mol) of sodium carbonate and 300 ml of acetonitrile is refluxed for 10 hours. Then the reaction mixture is filtered and the filtrate is evaporated to dryness in vacuo. The crude product obtained is purified by chromatography on silica gel (Baker, 30–60 μm) with a mixture of methylene chloride/methanol/cyclohexane/ammonia/ethyl acetate=68:15:15:2:500 as eluant.
Colourless crystals of m.p. 115°–130° C.
Yield: 3.8 g (25 of theory).

EXAMPLE 9

5,11-Dihydro-11-[[4-[3-[(2,2-dimethyl-1-oxopentyl)-ethylamino]propyl]-1-piperidinyl]acetyl]-6H-pyrido-[2,3-b][1,4]benzodiazepin-6-one Prepared analogously to Example 1 from 5,11-dihydro-11-[[4-[3-(ethylamino)propyl]1-piperidinyl]acetyl]-6H-pyrido[2,3-b][1,4]benzodiazepin-6-one and 2,2-dimethylvaleric acid chloride in a yield of 62% of theory.
Colourless crystals of m.p. 138°–140°C. (diethylether).

EXAMPLE 10

5,11-Dihydro-8-chloro-11-[[4-[3-[(2,2-dimethyl-1-oxopropyl)ethylamino]propyl]-1-piperidinyl]acetyl]-6H-pyrido[2,3-b ][1,4]benzodiazepin-6-one Prepared analogously to Example 1 from 5,11-dihydro-8-chloro-11-[[4-[3-(ethylamino)propyl]-1-piperidinyl]-acetyl]-6H-pyrido[2,3-b][1,4]benzodiazepin-6-one and pivalic acid chloride in a yield of 77% of theory.
Colourless crystals of m.p. 168°–170° C. (ethyl acetate).

EXAMPLE 11

5,11-Dihydro-8-chloro-11-[[4-[3-[(2,2-dimethyl-1-oxobutyl)-ethylamino]propyl]-1-piperidinyl]acetyl]-6H-pyrido[2,3-b][1,4]benzodiazepin-6-one Prepared analogously to Example 1 from 5,11-dihydro-8-chloro-11-[[4-[3-(ethylamino)propyl]-1-piperidinyl]-acetyl]-6H-pyrido[2,3-b][1,4]benzodiazepin-6-one and 2,2-dimethylbutyric acid chloride in a yield of 36% of theory.
Colourless crystals of m.p. 173°–174° C. (diisopropylether).

EXAMPLE 12

5,11-Dihydro-8-chloro-11-[[4-[3-[(2,2-dimethyl-1-oxopentyl)-ethylamino]propyl]1-piperidinyl]acetyl ]-6H-pyrido[2,3-b][1,4]benzodiazepin-6-one Prepared analogously to Example 1 from 5,11-dihydro-8-chloro-11-[[4-[3-(ethylamino)propyl]-1-piperidinyl]-acetyl]-6H-pyrido[2,3-b][1,4]benzodiazepin-6-one and 2,2-dimethylvaleric acid chloride in a yield of 70%.
Colourless crystals of m.p. 172°–173° C. (ethyl acetate).

EXAMPLE 13

5,11-Dihydro-8-chloro-11-[[4-[3-[(cyclopropylcarbonyl)-ethylamino]propyl]-1-piperidinyl]acetyl]-6H-pyrido[2,3-b][1,4]benzodiazepin-6-one Prepared analogously to Example 1 from 5,11-dihydro-8-chloro-11-[[4-[3-(ethylamino)propyl]-1-piperidinyl]-acetyl]-6H-pyrido[2,3-b][1,4]benzodiazepin-6-one and cyclopropanecarboxylic acid chloride in a yield of 76% of theory.
Colourless crystals of m.p. 136°–138° C. (diethylether/ethyl acetate).

EXAMPLE 14

5,11-Dihydro-8-methyl-11-[[4-[3-[(2,2-dimethyl-1-oxopropyl)-ethylamino]propyl]-1-piperidinyl]acetyl]-6H-pyrido[2,3-b][1,4]benzodiazepin-6-one Prepared analogously to Example 1 from 5,11-dihydro-8-methyl-11-[[4-[3-(ethylamino)propyl]-1-piperidinyl]-acetyl]-6H-pyrido[2,3-b][1,4]benzodiazepin-6-one and pivalic acid chloride in a yield of 23% of theory.
Colourless crystals of m.p. 177°–179 ° C. (acetonitrile).

EXAMPLE 15

5,11-Dihydro-9-chloro-11-[[4-[3-[(2,2-dimethyl-1-oxopentyl)-ethylamino]propyl]-1-piperidinyl]acetyl ]-6H-pyrido[2,3-b][1,4]benzodiazepin-6-one Prepared analogously to Example 1 from 5,11-dihydro-9-chloro-11-[[4-[3-(ethylamino) propyl]-1-piperidinyl]-acetyl]-6H-pyrido[2,3-b][1,4]benzodiazepin-6-one and 2,2-dimethylvaleric acid chloride. Purification was carried out by chromatography on silica gel (Merck 30–60 μm) using a mixture of ethyl acetate/ammonia (10:0.1) as eluant.
Yield: 48% of theory.

Colourless crystals of m.p. 150°–152° C. (diethylether).

EXAMPLE 16

5,11-Dihydro-9-chloro-11-[[4-[3-[(2,2-dimethyl-1-oxobutyl)-ethylamino]propyl]-1-piperidinyl]acetyl]-6H-pyrido[2,3-b][1,4]benzodiazepin-6-one Prepared analogously to Example 1 from 5,11-dihydro-9-chloro-11-[[4-[3-(ethylamino)propyl]-1-piperidinyl]-acetyl]-6H-pyrido[2,3-b][1,4]benzodiazepin-6-one and 2,2-dimethylbutyric acid chloride. The base was purified by chromatography on silica gel (Merck, 30–60 μm) using a mixture of ethyl acetate/ammonia (10:0.1).
Yield: 54% of theory.
Colourless crystals of m.p. 123°–125° C. (diethylether).

EXAMPLE 17

5,11-Dihydro-8-methyl-11-[[4-[3-[(2,2-dimethyl-1-oxo-butyl)ethylamino]propyl]-1-piperidinyl]acetyl]-6H-pyrido[2,3-b][1,4]benzodiazepin-6-one Prepared analogously to Example 1 from 5,11-dihydro-8-methyl-11-[[4-[3-(ethylamino)propyl]-1-piperidinyl]-acetyl]-6H-pyrido[2,3-b][1,4]benzodiazepin-6-one and 2,2-dimethylbutyric acid chloride. Purification was carried out by chromatography on silica gel (Baker, 30–60 μm) using a mixture of ethyl acetate/ammonia (10:0.1) as eluant.
Yield: 41% of theory.
Colourless crystals of m.p. 97°–99° C. (ethyl acetate).

EXAMPLE 18

5,11-Dihydro-8-methyl-11-[[4-[3-[(2,2-dimethyl-1-oxopentyl)ethylamino]propyl]-1-piperidinyl]acetyl]-6H-pyrido[2,3-b][1,4]benzodiazepin-6-one Prepared analogously to Example 1 from 5,11-dihydro-8-methyl-11-[[4-[3-(ethylamino)propyl]-1-piperidinyl]-acetyl]-6H-pyrido[2,3-b][1,4]benzodiazepin-6-one and 2,2-dimethylvaleric acid chloride. Purification by chromatography on silica gel (Baker, 30–60 μm) using a mixture of ethyl acetate/ammonia (10:0.1) as eluant.
Yield: 28% of theory.
Colourless crystals of m.p. 83°–85° C. (ethyl acetate).

EXAMPLE 19

5,11-Dihydro-8-chloro-11-[[4-[3-[(2,2-dimethyl-1-oxo-4-penten-1yl)-ethylamino]propyl]-1-piperidinyl]acetyl]-6H-pyrido[2,3-b][1,4]benzodiazepin-6-one Prepared analogously to Example 1 from 2,2-dimethyl-4-pentenoic acid chloride and 5,11-dihydro-8-chloro-11-[[4-[3-(ethylamino)propyl]-1-piperidinyl]acetyl]-6H-pyrido[2,3-b][1,4]benzodiazepin-6-one. Purification by chromatography on silica gel (Baker, 30–60 μm) using a mixture of ethyl acetate/methanol/cyclohexane/ammonia=8:1:1:0.1 as eluant.
Yield: 88% of theory.
Colourless crystals of m.p. 157°–158° C. (diethylether).

EXAMPLE 20

5,11-Dihydro-8-chloro-11-[[4-[3-[(cyclohexylcarbonyl)-ethylamino]propyl]-1-piperidinyl]acetyl]-6H-pyrido[2,3-b][1,4]benzodiazepin-6-one Prepared analogously to Example 1 from 5,11-dihydro-8-chloro-11-[[4-[3-(ethylamino)propyl]-1-piperidinyl]-acetyl]-6H-pyrido[2,3-b][1,4]benzodiazepin-6-one and cyclohexanecarboxylic acid chloride. Purification was carried out by chromatography on silica gel (Baker, 30–60 μm) using a mixture of ethyl acetate/methanol/cyclohexane/ammonia=8:1:1:0.1 as eluant.
Yield: 70% of theory.
Colourless crystals of m.p. 162°–163° C. (diethylether).

EXAMPLE 21

5,11-Dihydro-8-chloro-11-[[4-[3-[(1-oxopentyl)-ethylamino]propyl]-1-piperidinyl]acetyl]-6H-pyrido[2,3-b][1,4]benzodiazepin-6-one Prepared analogously to Example 1 from 5,11-dihydro-8-chloro-11-[[4-[3-(ethylamino)propyl]-1-piperidinyl]-acetyl]-6H-pyrido[2,3-b][1,4]benzodiazepin-6-one and valeric acid chloride. Purification was carried out by chromatography on silica gel (Baker, 30–60 μm) using a mixture of ethyl acetate/methanol/cyclohexane/ammonia=8:1:1:0.1 as eluant.
Yield: 73% of theory.
Colourless crystals of m.p. 150°–152° C. (diethylether).

EXAMPLE 22

5,11-Dihydro-8-chloro-11-[[4-[3-[(1-oxobutyl)ethyl-amino]propyl]-1-piperidinyl]acetyl]-6H-pyrido[2,3-b]-[1,4]benzodiazepin-6-one Prepared analogously to Example 1 from 5,11-dihydro-8-chloro-11-[[4-[3-(ethylamino)propyl]-1-piperidinyl]acetyl]-6H-pyrido[2,3-b][1,4]benzodiazepin-6-one and butyric acid chloride. Purification by chromatography on silica gel analogously to Example 21.
Yield: 75% of theory.
Colour less crystals of m.p. 152°–154° C. (diethylether).

EXAMPLE 23

5,11-Dihydro-8-chloro-11-[[4-[3-[(1-oxopropyl)-ethylamino]propyl]-1-piperidinyl]acetyl]-6H-pyrido[2,3-b][1,4]benzodiazepin-6-one Prepared analogously to Example 1 from 5,11-dihydro-8-chloro-11-[[4-[3-(ethylamino)propyl]-1-piperidinyl]-acetyl]-6H-pyrido[2,3-b][1,4]benzodiazepin-6-one and propionic acid chloride. Purification by chromatography on silica gel analogously to Example 21.
Yield: 77% of theory.
Colourless crystals of m.p. 141°–143° C. (diethylether).

EXAMPLE 24

5,11-Dihydro-11-[[4-[3-[(1-oxopropyl)ethylamino]-propyl]-1-piperidinyl]acetyl]-6H-pyrido[2,3-b][1,4]-benzodiazepin-6-one Prepared analogously to Example 1 from 5,11-dihydro-11-[[4-[3-(ethylamino)propyl]-1-piperidinyl]acetyl]-6H-pyrido[2,3-b][1,4]benzodiazepin-6-one and propionic acid chloride. Purification by chromatography on silica gel analogously to Example 21.
Yield: 50% of theory.
Colourless crystals of m.p. 123°–125° C. (diethylether).

EXAMPLE 25

5,11-Dihydro-11-[[4-[3-[(1-oxobutyl) ethylamino]-propyl]-1-piperidinyl]acetyl]-6H-pyrido[2,3-b][1,4]-benzodiazepin-6-one Prepared analogously to Example 1 from 5,11-dihydro-11-[[4-[3-(ethylamino)propyl]-1]-1-piperidinyl]acetyl]-6H-pyrido[2,3-b][1,4]benzodiazepin-6-one and butyric acid chloride. Purification by chromatography on silica gel analogously to Example 21.

Yield: 61% of theory.
Colourless crystals of m.p. 174°–175° C. (diethylether).

EXAMPLE 26

5,11-Dihydro-11-[[4-[3-[(1-oxopentyl)-ethylamino]-propyl]-1-piperidinyl]acetyl]-6H-pyrido[2,3-b][1,4]-benzodiazepin-6-one Prepared analogously to Example 1 from 5,11-dihydro-11-[[4-[3-(ethylamino)propyl]-1-piperidinyl]acetyl]-6H-pyrido[2,3-b][1,4]benzodiazepin-6-one and valeric acid chloride. Purification by chromatography on silica gel analogously to Example 21.
Yield: 64% of theory.
Colourless crystals of m.p. 167°–168° C. (diethylether).

EXAMPLE 27

5,11-Dihydro-8-chloro-11-[[4-[3-[(1-methylcyclohexyl-carbonyl)ethylamino]propyl-1-piperidinyl]acetyl]-6H-pyrido[2,3-b][1,4]benzodiazepin-6-one A solution of 313 mg (2.2 mMol) of 1-methylcyclohexane-carboxylic acid and 340 mg (3.0 mMol) of N,N'-carbonyldiimidazole in 20 ml of tetrahydrofuran is heated to 45° C. for 1 hour with stirring. Then 920 mg (2 mMol) of 5,11-dihydro-8-chloro-[[4-[3-(ethylamino)-propyl]-1-piperidinyl]acetyl]-6H-pyrido[2,3-b][1,4]-benzodiazepin-6-one are added and the reaction solution is stirred for a further two hours at 45° C. After the reaction has ended the reaction mixture is poured into a saturated sodium chloride solution, the organic phase is separated off and evaporated to dryness in vacuo. The residue obtained is distributed between water and ethyl acetate and the ethyl acetate phase is then evaporated down in vacuo. The crude product obtained is purified on silica gel (Baker, 30–60 µm) by chromatography using a mixture consisting of ethyl acetate/methanol/ammonia (9:1:0.1). The desired compound is obtained as an amorphous product in a yield of 130 mg (11% of theory).
$R_f$ value in the thin layer chromatogram: 0.4 (TLC plates: silica gel made by Merck; eluant: methylene chloride/cyclohexane/methanol/ammonia=680:150:150:20).

EXAMPLE 28

5,1-Dihydro-8-chloro-11-[4-[3-[(tricyclo[3,3,1,1$^{3,7}$]dec-1-ylcarbonyl)ethylamino]propyl]-1-piperidinyl]acetyl]-6H-pyrido[2,3-b][1,4]benzodiazepin-6-one Prepared analogously to Example 1 from 5,11-dihydro-8-chloro-11-[[4-[3-(ethylamino)propyl]-1-piperidinyl]-acetyl]-6H-pyrido[2,3-b][1,4]benzodiazepin-6-one and tricyclo[3,3,1,1$^{3,7}$]decane-1-carboxylic acid chloride in a yield of 20% of theory. Purification by chromatography on silica gel (Baker) using a mixture of ethyl acetate/cyclohexane/methanol/ammonia=80:10:10:1 as eluant.
$R_f$ value in the thin layer chromatogram: 0.65 (TLC plates: silica gel made by Merck; eluant: methylene chloride/cyclohexane/methanol/ammonia=680:150:150:20).

EXAMPLE 29

5,11-Dihydro-11-[[4-[4-[(2,2-dimethyl -1-oxopropyl)-ethylamino]butyl]-1-piperidinyl]acetyl]-6H-pyrido-[2,3-b ][1,4]benzodiazepin-6-one Prepared analogously to Example 1 from 5,11-dihydro-11-[[4-[4-(ethylamino)butyl]-1-piperidinyl]acetyl]-6H-pyrido[2,3-b][1,4]benzodiazepin-6-one and pivalic acid chloride in a yield of 62% of theory.
Colourless crystals of m.p. 206°–207° C. (ethyl acetate).

EXAMPLE 30

5,1-Dihydro-11-[[4-[4-[(cyclopropylcarbonyl)-ethylamino]butyl]-1-piperidinyl]acetyl]-6H-pyrido-[2,3-b][1,4]benzodiazepin-6-one Prepared analogously to Example 1 from 5,11-dihydro-11-[[4-[4(ethylamino)butyl]-1-piperidinyl]acetyl]-6H-pyrido[2,3-b][1,4]benzodiazepin-6-one and cyclopropane carboxylic acid chloride in a yield of 67% of theory.
Colourless crystals of m.p. 202°–204° C. (ethyl acetate).

EXAMPLE 31

5,11-Dihydro-11-[[4-[4-[(2,2-dimethyl-1-oxobutyl)-ethylamino]butyl]-1-piperidinyl]acetyl]-6H-pyrido[2,3-b][1,4]benzodiazepin-6-one Prepared analogously to Example 1 from 5,11-dihydro-11-[[4-[4(ethylamino)butyl]-1-piperidinyl]acetyl]-6H-pyrido[2,3-b][1,4]benzodiazepin-6-one and 2,2-dimethylbutyric acid chloride in a yield of 64% of theory.
Colourless crystals of m.p. 153°–155° C. (diethylether).

EXAMPLE 32

5,11-Dihydro-11-[[4-[4-[(2,2-dimethyl-1-oxopentyl)-ethylamino]butyl]-1-piperidinyl]acetyl]-6H-pyrido[2,3-b][1,4]benzodiazepin-6-one Prepared analogously to Example 1 from 5,11-dihydro-11-[[4-[4-(ethylamino)butyl]-1-piperidinyl]acetyl]-6H-pyrido[2,3-b][1,4]benzodiazepin-6-one and 2,2-dimethyl-valeric acid chloride in a yield of 69% of theory.
Colourless crystals of m.p. 168°–169° C. (ethyl acetate).

EXAMPLE 33

5,11-Dihydro-11-[[4-[4-[(3,4-dimethoxybenzoyl)-ethylamino]butyl]-1-piperidinyl]acetyl]-6H-pyrido-[2,3-b][1,4]benzodiazepin-6-one Prepared analogously to Example 1 from 5,11-dihydro-11-[[4-[4-(ethylamino)butyl]-1-piperidinyl]acetyl]-6H-pyrido[2,3-b][1,4]benzodiazepin-6-one and 3,4-dimethoxybenzoic acid chloride in a yield of 67% of theory.
Colourless crystals of m.p. 132°–135° C. (ethyl acetate).

EXAMPLE 34

5,11-Dihydro-8-chloro-11-[[4-[4-[(2,2-dimethyl-1-oxopropyl)ethylamino]butyl]-1-piperidinyl]acetyl]-6H-pyrido[2,3-b ][1,4]benzodiazepin-6-one Prepared analogously to Example 1 from 5,11-dihydro-8-chloro-11-[[4-[4-(ethylamino)butyl]-1-piperidinyl]-acetyl]-6H-pyrido[2,3-b][1,4]benzodiazepin-6-one and pivalic acid chloride in a yield of 55% of theory.
Colourless crystals of m.p. 205°–207° C. (ethyl acetate).

EXAMPLE 35

5,11-Dihydro-8-chloro-11-[[4-[4-[(2,2-dimethyl-1-oxopentyl)ethylamino]butyl]-1-piperidinyl]acetyl]-6H-pyrido-[2,3-b]-[1,4]benzodiazepin-6-one Prepared analogously to Example 1 from 5,11-dihydro-8-chloro-11-[[4-[4-(ethylamino)butyl]-1-piperidinyl]-acetyl]-6H-pyrido[2,3-b][1,4]benzodiazepin-6-one and 2,2-dimethylvaleric acid chloride in a yield of 60% of theory.
colourless crystals of m.p. 149°–151° C. (ethyl acetate).

EXAMPLE 36

4,9-Dihydro-3-methyl-4-[[4-[3-[(2,2-dimethyl-1-oxobutyl)-ethylamino]propyl]-1-piperidinyl]acetyl]-10H-thieno[3,4-b][1,5]benzodiazepin-10-one Prepared analogously to Example 1 from 4,9-dihydro-3-methyl-4-[[4-[3-(ethylamino)propyl]-1-piperidinyl]-acetyl]-10H-thieno[3,4-b][1,5]benzodiazepin-10-one and 2,2-dimethylbutyric acid chloride in a yield of 19% of theory.
Colourless crystals of m.p. 207°–208° C. (acetonitrile).

EXAMPLE 37

4,9-Dihydro-3-methyl-4-[[4-[3-[(2,2-dimethyl-1-oxopropyl)-ethylamino]propyl]-1-piperidinyl]acetyl]-10 H-thieno[3,4-b][1,5]benzodiazepin-10-one Prepared analogously to Example 1 from 4,9-dihydro-3-methyl-4-[[4-[3-(ethylamino)propyl]-1-piperidinyl]-acetyl]-10H-thieno[3,4-b][1,5]benzodiazepin-10-one and pivalic acid chloride in a yield of 29% of theory.
Colourless crystals of m.p. 188°–189° C. (acetonitrile).

EXAMPLE 38

5,11-Dihydro-11-[[4-[2-[(benzoyl)methylamino]ethyl]-1-piperidinyl]acetyl]-6H-pyrido[2,3-b][1,4]benzodiazepin-6-one Prepared analogously to Example 1 from 5,11-dihydro-11-[[4-[2-(methylamino)ethyl]-1-piperidinyl]acetyl]-6H-pyrido[2,3-b][1,4]benzodiazepin-6-one and benzoylchloride in a yield of 80% of theory.
Colourless crystals of m.p. 120°–122° C. (ethyl acetate).

EXAMPLE 39

5,11-Dihydro-11-[[4-[[(acetyl)methylamino]methyl]-1-piperidinyl]acetyl]-6H-pyrido[2,3-b][1,4]benzodiazepin-6-one Prepared analogously to Example 1 from 5,11-dihydro-11-[[4-[(methylamino)methyl]-1-piperidinyl]acetyl]-6H-pyrido[2,3-b][1,4]benzodiazepin-6-one and acetyl chloride in yield of 83% of theory.
Colourless crystals of m.p. 242°–243° C. (ethyl acetate).

EXAMPLE 40

3-Chloro-4-[[4-[3-[(2,2-dimethyl-1-oxopropyl)ethylamino]propyl]-1-piperidinyl]acetyl]-1-methyl-1,4,9,10-tetrahydropyrrolo[3,2-b][1,5]benzodiazepin-10-one Prepared analogously to Example 1 from 3-chloro-4-[[4-[3-(ethylamino)propyl]-1-piperidinyl]acetyl]-1-methyl-1,4,9,10-tetrahydropyrrolo[3,2-b][1,5]benzodiazepin-10-one and pivalic acid chloride in a yield of 42% of theory.
Colourless crystals of m.p. 150°–151° C. (ethyl acetate).

EXAMPLE 41

6,11-Dihydro-11-[[4-[3-[(2,2-dimethyl-1-oxopentyl)-ethylamino]propyl]-1-piperidinyl]acetyl]-5H-pyrido-[2,3-b][1,5]benzodiazepin-5-one Prepared analogously to Example 1 from 6,11-dihydro-11-[[4-[3-(ethylamino)propyl]-1-piperidinyl]acetyl-5H-pyrido[2,3-b][1,5]benzodiazepin-5-one and 2,2-dimethylvaleric acid chloride in a yield of 44%.
$R_f$ value in the thin layer chromatogram: 0.6 (TLC plates: silica gel, Merck; eluant:methylene chloride/cyclohexane/methanol/ammonia=6.8:1.5:1.5:0.2).

EXAMPLE 42

5,11-Dihydro-8-chloro-11-[[4-[3-[(2,2-dimethyl-1-oxopentyl)-ethylamino]propyl]-1-piperidinyl]acetyl]-6H-pyrido[2,3-b][1,4]benzodiazepin-6-one In a solution of 0.52 g (4 mMol) of 2,2-dimethylvaleric acid and 0.54 g (4 mMol) of 1-hydroxybenzotriazole in 50 ml of tetrahydrofuran, 0.82 g (4 mMol) of N,N'-dicyclohexylcarbodiimide are added, with stirring, at 0° C. The mixture is stirred for a further 30 minutes at the same temperature and then 1.8 g (4 mMol) of 5,11-dihydro-11-[[4-[3-(ethylamino)propyl]-1-piperidinyl]-acetyl]-6H-pyrido[2,3-b][1,4]benzodiazepin-6-one are added. The mixture is stirred for a further 12 hours at ambient temperature. The dicyclohexylurea formed is removed by suction filtering and the filtrate is evaporated to dryness in vacuo. The residue is purified by chromatography on silica gel (Baker) using a mixture of ethyl acetate/methanol/cyclohexane/ammonia= 8:1:1:0.1 as eluant. Colourless crystals of m.p. 172°–173° C. (ethyl acetate) are obtained.
Yield: 160 mg=7% of theory.
According to its physical-chemical and spectroscopic data the substance is completely identical to the substance obtained according to Example 12.

EXAMPLE 43

5,11-Dihydro-11-[[3-[3-[(benzoyl)methylamino]propyl]-1-piperidinyl]acetyl]-6H-pyrido[2,3-b][1,4]benzodiazepin-6-one Prepared analogously to Example 8 from 11-(chloroacetyl)-5,11-dihydro-6H-pyrido[2,3-b][1,4]-benzodiazepin-6-one and 3-[3-[(benzoyl)methylamino]-propyl]piperidine. Purification is carried out by chromatography on silica gel using a mixture of methylene chloride/methanol=99:1 as eluant.
Yield: 43% of theory.
Colourless crystals of m.p. 172°–173° C.

EXAMPLE 44

5,11-Dihydro-11-[[3-[3-[(acetyl)methylamino]propyl]-1-piperidinyl]acetyl]-6H-pyrido[2,3-b][1,4]benzodiazepin-6-one Prepared analogously to Example 8 from 11-(chloroacetyl)-5,11-dihydro-6H-pyrido[2,3-b][1,4]-benzodiazepin-6-one and 3-[3-[(acetyl)methylamino]-propyl]piperidine. Purification is carried out by chromatography on silica gel (Baker) using methylene chloride to which increasing amounts of methanol are added.
Yield: 23 % of theory.
Colourless crystals of m.p. 170°–172 ° C.

EXAMPLE 45

5,11-Dihydro-11-[[4-[3-[(2,2-dimethyl-1-oxopentyl)-amino]propyl]-1-piperidinyl]acetyl]-6H-pyrido[2,3-b]-[1,4]benzodiazepin-6-one Prepared analogously to Example 1 from 5,11-dihydro-11-[[4-(3-aminopropyl)-1-piperidinyl]acetyl]-6H-pyrido[2,3-b][1,4]benzodiazepin-6-one and 2,2-dimethyl-valeric acid chloride in a yield of 64% of theory.
Colourless crystals of m.p. 150°–152° C. (ethyl acetate).

EXAMPLE 46

5,10-Dihydro-5-[[4-[3-[(2,2-dimethyl-1-oxopentyl)-ethylamino]propyl]-1-piperidinyl]acetyl]-11H-dibenzo[b,e][1,4]diazepin-11-one Prepared analogously to Example 1 from 5,10-dihydro-5-[[4-[3-ethylamino]propyl]-1-piperidinyl]acetyl]-11H-dibenzo[b,e][1,4]diazepin-11-one.
Purification is carried out by chromatography on silica gel (Merck, 30–60 μm) using a mixture of ethyl acetate/ammonia (10:0.1) as eluant.
Yield: 53% of theory.
Colourless crystals of m.p. 124°–126° C. (diethylether).

$R_f$ value in the thin layer chromatogram: 0.5 (TLC plates: silica gel, made by Merck; eluant: methylene chloride/ cyclohexane/methanol/ammonia=6.8:1.5:1.5:0.2).

The following Examples illustrate the preparation of some pharmaceutical administration forms:

EXAMPLE I

Tablets containing 5 mg of 5,11-dihydro-11-[[4-[3-[(2,2-dimethyl)-1-oxobutyl)ethylamino]propyl]-1-piperidinyl] acetyl]-6H-pyrido[2,3-b][1,4]benzodiazepin-6-one
Composition:
1 tablet contains:

| Active substance | 5.0 mg |
|---|---|
| Lactose | 148.0 mg |
| Potato starch | 65.0 mg |
| Magnesium stearate | 2.0 mg |
| | 220.0 mg |

Method of Preparation

A 10% mucilage is prepared from potato starch by heating. The active substance, lactose and the remaining potato starch are mixed together and granulated with the above mucilage through a 1.5 mm mesh screen. The granules are dried at 45° C., rubbed through the same screen again, mixed with magnesium stearate and compressed to form tablets.
Weight of tablet: 220 mg
Punch: 9 mm

EXAMPLE II

Coated tablets containing 5 mg of 5,11-dihydro-11-[[4-[3-[(2,2-dimethyl)-1-oxobutyl) ethylamino]propyl]-1-piperidinyl]acetyl]-6H-pyrido[2,3-b][1,4]benzodiazepin-6-one The tablets prepared according to Example I are coated, by a known method, with a coating consisting essentially of sugar and talc. The finished coated tablets are polished with beeswax.
Weight of coated tablet: 300 mg

EXAMPLE III

Ampoules containing 10 mg of 5,11-dihydro-11-[[4-[4-[(2,2-dimethyl)-1-oxopentyl) ethylamino]butyl]-1-piperidinyl]acetyl]-6H-pyrido[2,3-b][1,4]benzodiazepin-6-one dihydrochloride
Composition:
1 ampoule contains:

| Active substance | 10.0 mg |
|---|---|
| Sodium chloride | 8.0 mg |
| Distilled water | ad 1 ml |

Method of Preparation

The active substance and sodium chloride are dissolved in distilled water and then made up to the volume specified. The solution is sterile filtered and transferred into 1 ml ampoules. Sterilisation: 20 minutes at 120° C.

EXAMPLE IV

Suppositories containing 20 mg of 5,11-dihydro-8-chloro-11-[[4-[3-[(2,2-dimethyl-1-oxopentyl)ethyl-amino]propyl]-1-piperidinyl]acetyl]-6H-pyrido[2,3-b]-[1,4]benzodiazepin-6-one
Composition:

1 suppository contains:

| Active substance | 20.0 mg |
|---|---|
| Suppository mass (e.g. Witepsol W 45®) | 1680.0 mg |
| | 1700.0 mg |

Method of Preparation

The finely powdered active substance is suspended in the molten suppository mass which has been cooled to 40° C. The mass is poured at 37° C. into slightly chilled suppository moulds.
Weight of suppository 1.7 g

EXAMPLE V

Drops containing 5,11-dihydro-11-[[4-[4-[(2,2-dimethyl)-1-oxopentyl) ethylamino]butyl]-1-piperidinyl]acetyl]-6H-pyrido[2,3-b][1,4]benzodiazepin-6-one
Composition:
100 ml of drops solution contain:

| Methyl p-hydroxybenzoate | 0.035 g |
|---|---|
| Propyl p-hydroxybenzoate | 0.015 g |
| Aniseed oil | 0.05 g |
| Menthol | 0.06 g |
| Pure ethanol | 10.0 g |
| Active substance | 0.5 g |
| Sodium cyclamate | 1.0 g |
| Glycerol | 15.0 g |
| Distilled water | ad 100.0 ml |

Method of Preparation

The active substance and sodium cyclamate are dissolved in about 70 ml of water and glycerol is added. The p-hydroxybenzoates, aniseed oil and menthol are dissolved in ethanol and this solution is added with stirring to the aqueous solution. Finally, the solution is made up to 100 ml with water and filtered to remove any suspended particles.

What is claimed is:

1. A method for treating or inhibiting memory deterioration caused by impaired release of acetylcholine, which method comprises administering to a patient in need of such treatment a therapeutically effective amount of a compound of the formula wherein X is a =CH— group or a nitrogen atom, n represents the number 3 or 4, $R^1$ is a straight-chained $C_{1-4}$ alkyl group, $R^2$ is a branched $C_{4-6}$ alkyl group, a cyclopropyl, cyclobutyl, cyclopentyl, cyclohexyl, cycloheptyl, methylcyclopentyl, methylcyclohexyl, methylcycloheptyl or adamantyl group, $R^3$ and $R^4$ represent hydrogen atoms or one of these groups represents a methyl group or a halogen atom, or a pharmaceutically acceptable salt thereof with an inorganic or organic acid.

2. The method of claim 1, wherein $R^1$ represents an ethyl group.

3. A method for treating or inhibiting memory deterioration caused by impaired release of acetylcholine, which method comprises administering to a patient in need of such treatment a therapeutically effective amount of a compound selected from the group consisting of:

5,11-dihydro-11-[[4-[3-[(2,2-dimethyl-1-oxobutyl)-ethylamino]-propyl]-1-piperidinyl]acetyl]-6H-pyrido[2,3-b][1,4]benzodiazepin-6-one, 5,11-dihydro-[[4-[3-[(2,2-dimethyl-1-oxopentyl)-ethylamino]-1-piperidinyl]acetyl]-6H-pyrido[2,3-b][1,4]benzodiazepin-6-one, 5,11-dihydro-[[4-[4-[(2,2-dimethyl-1-oxopentyl)-ethylamino]butyl]-1-piperidinyl]acetyl]-6H-pyrido[2,3-b][1,4]benzodiazepin-6-one, 5,11-dihydro-8-chloro-11-[[4-[3-[(2,2-dimethyl-1-oxopentyl)-ethylamino]propyl]-1-piperidinyl]acetyl]-6H-pyrido[2,3-b]-[1,4]benzodiazepin-6-one, 5,11-dihydro-8-methyl-11-[[4-[3-[(2,2-dimethyl-1-oxopropyl)-ethylamino]propyl]-1-piperidinyl]acetyl]-6H-pyrido[2,3-b]-[1,4]benzodiazepin-6-one, 5,11-dihydro-11-[[4-[3-[(2,2-dimethyl-1-oxopropyl)-ethylamino]propyl]-1-piperidinyl]acetyl]-6H-pyrido[2,3-b][1,4]-benzodiazepin-6-one, 5,11-dihydro-8-methyl-11-[[4-[3-[(2,2-dimethyl-1-oxobutyl)-ethylamino]propyl]-1-piperidinyl]acetyl]-6H-pyrido[2,3-b]-[1,4]benzodiazepin-6-one, 5,10-dihydro-5-[[4-[3-[(2,2-dimethyl-1-oxopentyl)-ethylamino]propyl]-1-piperidinyl]acetyl]-11H-dibenzo[b,e][1,4]-diazepin-11-one, and pharmaceutically acceptable salts thereof.

4. A method for treating or inhibiting memory deterioration caused by impaired release of acetylcholine, which method comprises administering to a patient in need of such treatment a therapeutically effective amount of 5,11-dihydro-[[4-[3-[(2,2-dimethyl-1-oxopentyl)-ethylamino]propyl]-1-piperidinyl]acetyl]-6H-pyrido[2,3-b][1,4]benzodiazepin-6-one, or a pharmaceutically acceptable salt thereof with an inorganic or organic acid.

5. A method for treating or inhibiting memory deterioration caused by impaired release of acetylcholine, which method comprises administering to a patient in need of such treatment a therapeutically effective amount of 5,11-dihydro-8-chloro-11-[[4-[3-[(2,2-dimethyl-1-oxopentyl)-ethylamino]propyl]-1-piperidinyl]acetyl]-6H-pyrido[2,3-b]-[1,4]benzodiazepin-6-one, or a pharmaceutically acceptable salt thereof with an inorganic or organic acid.

6. A method for treating or inhibiting memory deterioration caused by impaired release of acetylcholine, which method comprises administering to a patient in need of such treatment a therapeutically effective amount of 5,10-dihydro-5-[[4-[3-[(2,2-dimethyl-1-oxopentyl)-ethylamino]propyl]-1-piperidinyl]acetyl]-11H-dibenzo[b,e][1,4]diazepin-11-one, or a pharmaceutically acceptable salt thereof with an inorganic or organic acid.

\* \* \* \* \*